(12) United States Patent
Eloy

(10) Patent No.: US 6,275,045 B1
(45) Date of Patent: Aug. 14, 2001

(54) MICROWAVE TRANSMITTER-RECEIVER

(75) Inventor: Jean-François Eloy, Gradignan (FR)

(73) Assignee: Commissariat a l'Energie Atomique (FR)

( * ) Notice: Subject to any disclaimer, the term of this patent is extended or adjusted under 35 U.S.C. 154(b) by 0 days.

(21) Appl. No.: 09/319,978

(22) PCT Filed: Dec. 17, 1997

(86) PCT No.: PCT/FR97/02327

§ 371 Date: Jun. 14, 1999

§ 102(e) Date: Jun. 14, 1999

(87) PCT Pub. No.: WO98/27613

PCT Pub. Date: Jun. 25, 1998

(30) Foreign Application Priority Data

Dec. 18, 1996 (FR) .................................. 96 15568

(51) Int. Cl.[7] .................................................. G01N 22/00
(52) U.S. Cl. ............................................ 324/639; 324/637
(58) Field of Search ..................................... 324/637, 639

(56) References Cited

U.S. PATENT DOCUMENTS

| 4,855,749 | 8/1989 | DeFonzo | 343/767 |
| 5,056,111 | 10/1991 | Duling, III et al. | 375/37 |
| 5,128,621 | * | 7/1992 | Berthaud et al. | 324/639 |
| 5,719,664 | 2/1998 | Besesty et al. | 356/5.01 |
| 6,087,991 | * | 7/2000 | Kustas | 343/700 MS |

FOREIGN PATENT DOCUMENTS

| 0706063 | 4/1996 | (EP) | G01S/17/08 |
| 0727671 | 8/1996 | (EP) | G01R/31/265 |

OTHER PUBLICATIONS

Katzenellenbogen et al, Efficient generation of 380 fs pulses of THz radiation by ultra fast laser pulse excitation of a biased metal–semiconductor interface, Applied Physics Letters, vol. 58, No. 3 Jan. 21, 1991, pp. 222–224.

* cited by examiner

Primary Examiner—Glenn W. Brown
(74) Attorney, Agent, or Firm—Hayes, Soloway, Hennessey, Grossman & Hage PC

(57) ABSTRACT

Device for emission-reception of a stream of electromagnetic waves, in which an emission unit (1) and a reception unit (2) are each supplied with light energy passing through an optical guide (13). This light may be stopped by an optical gate (19). Otherwise, it reaches a micro-laser (4) that illuminates a photo-conducting sheet (5) on which an antenna (3) is located. The portions (6, 7) of the emitter antenna (3) at different potentials are then short circuited and a stream of electromagnetic waves is emitted. The wave stream passes through a medium to be studied and is returned to the receiving unit (2) in which it is sampled, recorded and analyzed to determine the composition of the medium through which it had passed. The wave stream has a wide frequency band and the opto-electronic device can be used to make a very compact system.

19 Claims, 5 Drawing Sheets

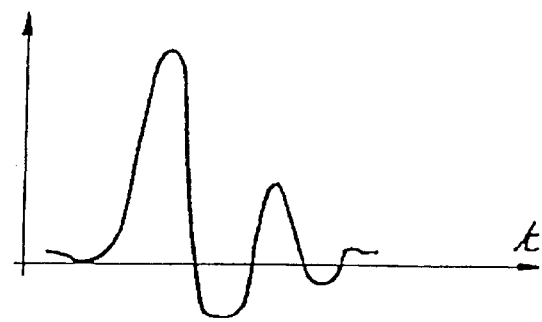
FIG. 4
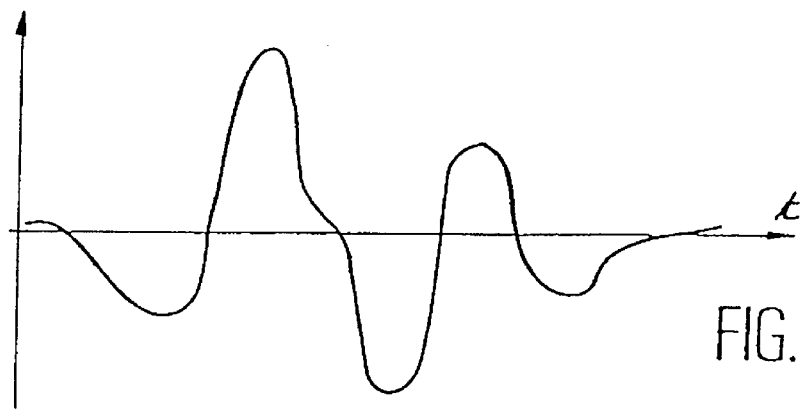
FIG. 5
FIG. 6
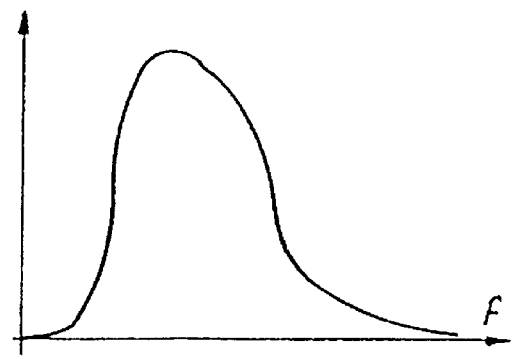
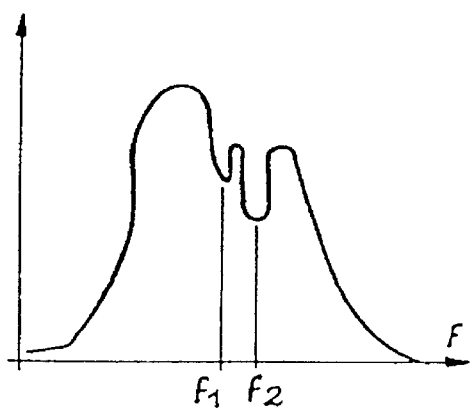
FIG. 7

MICROWAVE TRANSMITTER-RECEIVER

DESCRIPTION

This invention relates to a microwave emitter-receiver device.

It may be used for miscellaneous applications and particularly to monitor physical or chemical changes in a surrounding environment or to detect when an object passes. It is known that radiation passing through this environment is subject to disturbances that depend on its composition; the emitter then sends radiation in the form of a defined signal and the measurement consists of analyzing the signal received by the receiver after being modified by the medium through which it passes. These examination processes may be used continuously for applications in which risk areas are monitored and when carrying out tests; disturbances to environments through which radiation passes may be solid objects, or also and very frequently gasses, atmospheric pollutants, leakage gases, fire and firing plums. These devices may be used with measurement benches or with alarm beacons.

Infrared radiation, visible light and ultraviolet radiation have already been used with this type of device, but they have the disadvantage that they become inoperative under bad conditions; surrounding thermal radiation sources also produce infrared radiation that disturbs the measurements, and rain absorbs light radiation. These types of disturbances prevent detectors that analyze the received signal from seeing the signal.

Therefore it is preferred to use other wave types. Some systems include emission of a carrier wave within a restricted frequency range, which has the disadvantage that it only enables reduced observations. It is usually preferable to supply a wave stream extended over a wide frequency range, which imposes the use of a brief pulse so that a large proportion of the signal emitted is located in high frequencies. A recent illustration of a radar system with ultra-short pulses and a wide frequency range is given in the article by W. M. Boerner and J. S. Verdi "Polarimetric UWB Radar/ Sensing & Imaging" at the UWB-SP-2 Conference in Albuquerque in May 1996. Systems with electronic, opto-electronic or mixed triggering of the wave stream have been proposed.

The invention relates to an emitter-receiver device that can be used in high frequency spectroscopy (of the order of a gigahertz or a terahertz) and which has a particularly easy and compact design. It comprises an emitter and a receiver of electromagnetic waves with an antenna. The wave stream is triggered opto-electronically, using a light pulse generator system that illuminates a photo-conducting layer on which the emitter antenna is deposited or printed; a short circuit is created in the antenna which becomes active and emits the wave stream. Light pulses are also transmitted to the receiver, the receiver antenna being laid out in the same way on a photo-conducting layer, and also activates this receiving antenna so that it can collect the wave stream after it has passed through the environment being studied and then transmit it to means of recording or using the stream. The receiving antenna usually needs to be activated slightly after the emitting antenna to synchronize the process by absorbing the time necessary for the wave stream to pass between the antennas. A prior opto-electronic device that can be used for the same applications is described in U.S. Pat. No. 4,855,749 A, but it is not the same as the invention and its performances are much lower, as will be seen in more detail later.

All elements of the device may be placed on a single support board or on a small number of such boards, and a single electricity power supply is possible both for the emitting antenna and for control, usage and recording means, and for the light pulse generation means which could be a laser. In this case, its operation may be made discontinuous by an opto-electronic gate that chops its light radiation or by an element that varies the impedance of optical lines through which its light passes.

In its most general form, the invention relates to a wave emitter-receiver device to examine a medium through which the waves pass, comprising an emitter with an antenna and a receiver with an antenna, a wave generation device connected to the emitter, and a signal reception and usage device connected to the receiver; the antennas are formed of distinct portions and are laid out on a photo-conducting layer, the wave generation device comprises an electricity power supply initiating a potential difference between the portions of the emitter antenna, and the wave generation devices and signal reception and usage devices comprise means of supplying light pulses to the photo-conducting layers between the portions of the antennas; all this is similar to the device in U.S. Pat. No. 4,855,749, but the invention also involves the use of micro-lasers fixed on photo-conducting layers in order to form integrated receiver and emitter elements, whereas in the previous patent excitation is obtained by ordinary lasers which are large and difficult to adjust correctly. Note that with this type of opto-electronic device it is difficult to suitably transmit a wave stream due to its intensity and its frequency band. However the invention offers a device composed of emitter and receiver elements for which the adjustment will not change, due to the use of micro-lasers that are perfectly compatible with the stacks of photo-conducting layers. Another advantage is that these emitter and receiver elements may be moved without difficulty if the tests are to be carried out in different locations.

The invention will now be described in more detail using the following figures attached for illustrative and non-restrictive purposes, in order to better understand and describe other characteristics and qualities:

FIGS. 4 and 5 illustrate emitted and received wave streams;

FIGS. 6 and 7 illustrate use of these wave streams for measurement;

Figure 1:
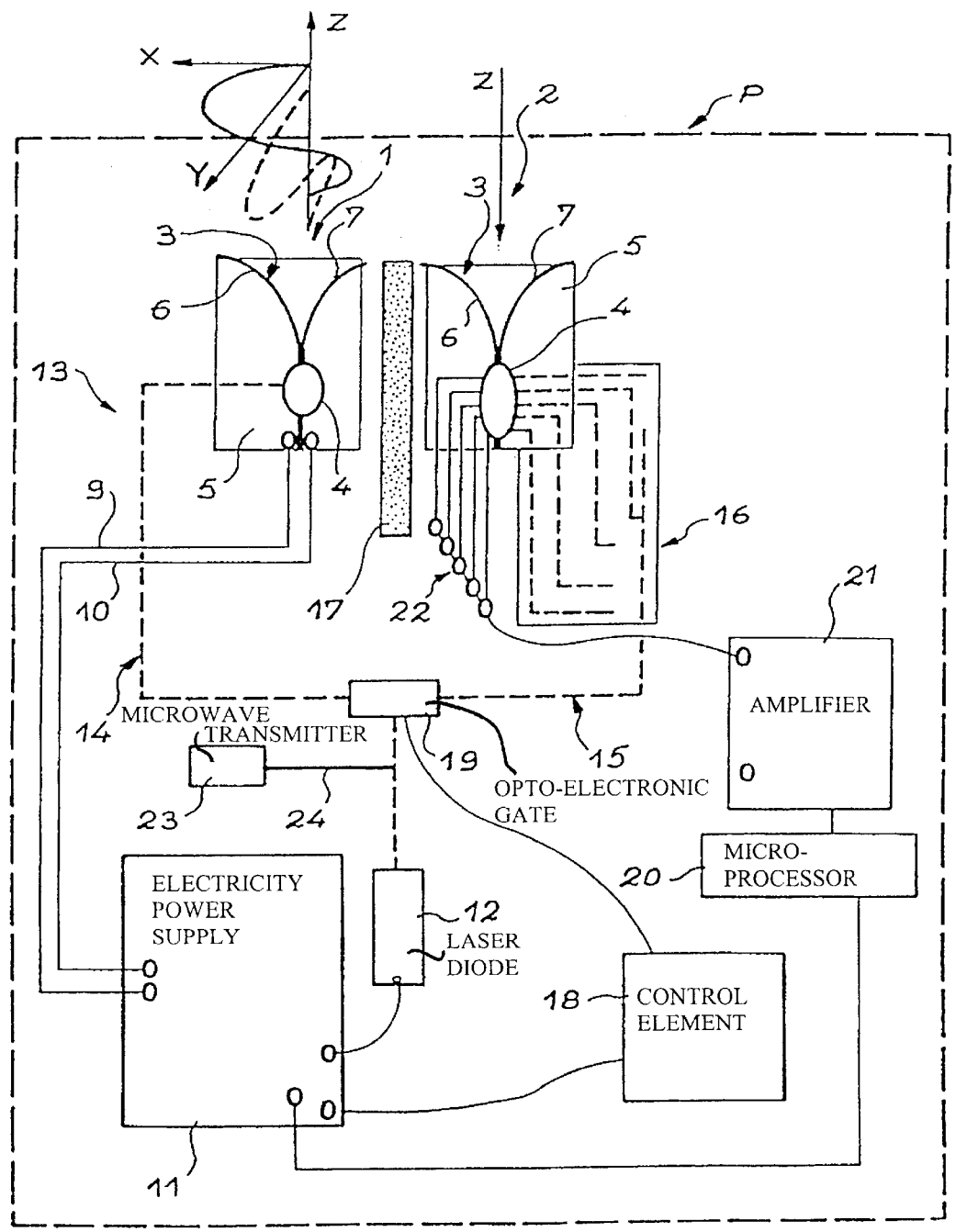
FIG. 1 is an overview of an embodiment of the invention.
Figure 8:
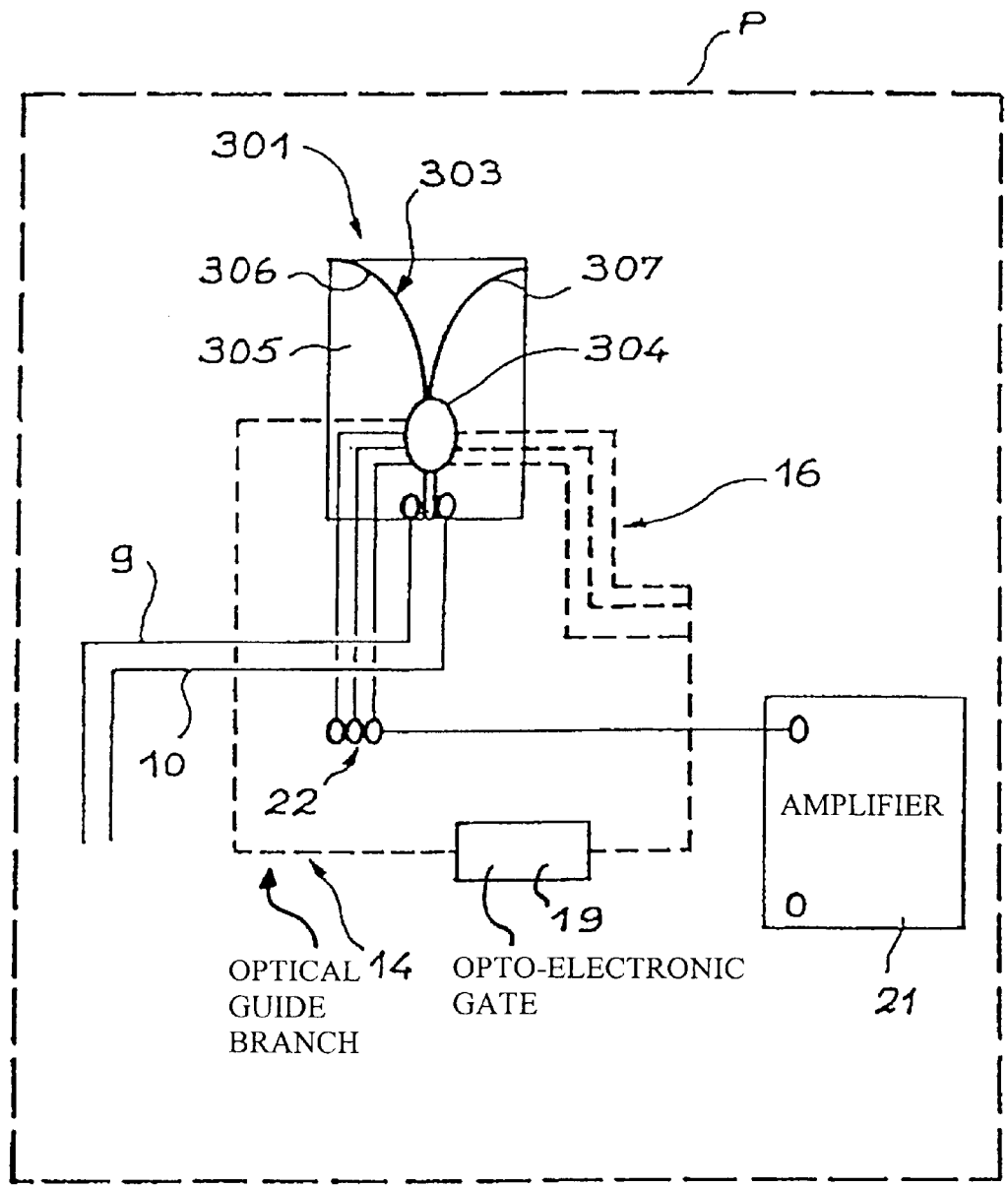

and FIG. 8 illustrates a variant of FIG. 1.

The variant embodiment in FIG. 1 was designed to measure signals reflected by the medium being studied. Therefore it comprises an emitter 1 and a receiver 2 placed side by side and in parallel, each of them having an antenna 3 pointing towards the front of the instrument, a micro-laser 4 located behind the antenna 3, and the assembly is placed on a sheet comprising a photo-conducting layer 5 as the upper layer which may be made of silicon doped with oxygen, or better cadmium telluride or gallium arsenide.

The antennas 3 are composed of at least two separate conducting parts 6 and 7 (made of aluminum or a chromium and gold alloy) deposited on the photo-conducting layer 5, the shape of which depends on the electromagnetic waves that they will be required to guide. In the case shown, they are in the shape of a parabola and the distance between them increases as the distance from micro-laser 4 increases. Spiral or other shaped antennas could be designed, as is well known. Parts 6 and 7 of the emitter antenna 3 are connected to two lines 9 and 10 respectively of a DC power supply 11, so that a potential difference can be imposed on them at all times. If the photo-conducting layer 5 is illuminated, it conducts electricity and a short circuit arises between the two parts 6 and 7 of antenna 3 which triggers emission of an electromagnetic wave stream.

The light radiation used for this purpose must excite the electrons in the atoms of the photo-conducting layer 5 so that they pass from the valence bands to the conducting band. This plasma can only be obtained if the radiation photons have sufficient energy to enable this excitation depending on the chemical nature of the photo-conducting layer 5.

The purpose of the micro-laser 4 is to provide the required illumination under good conditions. It is controlled by a laser diode 12 through an optical guide 13 including a fork, one branch 14 of the fork comprising a single line leading to the micro-laser 4 of the emitter 1; the other branch 15 of the optical guide 13 leads to the micro-laser 4 of receiver 2 and comprises optical delay lines 16 that can also illuminate the photo-conducting layer 5 and create a short circuit between parts 6 and 7 of the antenna 3, but with a delay. Since the delays of lines 16 are different, the antenna 3 of receiver 2 becomes active at different successive instants. Shielding 17 is placed between emitter 1 and receiver 2 to avoid electromagnetic interference between the two antennas 3.

The electricity power supply 11 supplies power to the various elements in the instrument including the laser diode 12 and a control element 18 used to adjust operation of an opto-electronic gate 19 located on the optical guide 13. This is a component such as a Pockels cell that can block off the optical guide 13 to light from the laser diode 12, or enable it to pass and touch the micro-lasers 4, according to an internal modification, for example concerning the refraction or extinguishing index which is imposed on it by an electric field or a polarization voltage set up in an adjacent crystal polarized by the electronic control 18. A microprocessor 20 also receives energy from the power supply 11 and is assigned more precisely to recording and analysis of signals received by the receiver 2, through an amplifier stage 21 and connection lines 22 leading to the micro-laser 4 of receiver 2. Finally, the electricity power supply 11 is connected to a microwave transmitter 23 which sends signal modulation microwaves output by the laser diode 12 through a guide 24 connected to the optical guide 13 (which may be of the Max-Zehnder type). This emitter 23 produces coupling between the light from laser diode 12 and the microwaves that it produces by modifying the impedance of the optical guide 13. Therefore it imposes a pulsed emission of light from the laser which makes the equipment operate in accordance with the pump-probe method for which the signal-to-noise ratio is higher.

However, the use of this emitter 23 is only optional, and other elements described above for this equipment could also be omitted or replaced.

The optical guide 13 could be replaced by an optical fibers network; the micro-lasers 4, assumed so far to be in direct optical contact with the photo-conducting layers 5 by being placed on these layers or on a transparent substrate of these layers, could be separated from each other by an optical concentration system.

It is possible and advantageous to place the instrument on an integrated circuit board P; otherwise, the receiver 2 and the emitter 1 could be placed on separate boards.

Therefore, the equipment operates when light from the laser diode 12 reaches the micro-lasers 4, with the opto-electronic gate 19 having been opened; the micro-laser 4 of the emitter 1 illuminates a portion of the photo-conducting layer 5 adjacent to parts 6 and 7 of the antenna 3 which creates a short circuit between them and emission of an electromagnetic wave stream through antenna 3 of emitter 1. This stream is reflected by the medium to be studied or by a mirror located behind this medium to antenna 3 of receiver 2. It is then collected in the form of an electric signal when the micro-laser 4 of the receiver 2, placed similarly to the micro-laser of emitter 1 with respect to the photo-conducting layer 5 and to parts 6 and 7 of antenna 3, puts these parts in short circuit; the current created by the wave stream passes through the connection lines 22, the amplifier stage 21 and ends up at the microprocessor 20. The device shown in FIG. 1 can be used to sample the received signal by means of optical delay lines 16 that illuminate the micro-laser 4 at successive instants and are therefore used to sample different portions of the received wave stream. Currents generated by these signal portions pass through the corresponding connection line 22 that stops in front of the optical delay line 16 active at that time.

The photo-diode 12 can emit continuously using the energy supplied by the electricity power supply 11, but this has no effect while the opto-electronic gate 19 is closed; it is decided to control this gate to periodically open it and thus emit a sequence of wave streams between which the signals can be received and recorded.

An operating variant consists of making the laser diode 12 emit in a pulsed manner by means of appropriate control of the electricity power supply by the control system 18.

Micro-lasers 4 can be integrated in the emitter 1 and the receiver, by making them fixed to the photo-conducting layers 5, so that they can be used easily and without making any adjustments to the position or the focal length, even if the emitter and the receiver are moved between two tests. Furthermore, micro-lasers are suitable for emitting very short duration wave streams, for example lasting 1 or 2 picoseconds, whereas durations of 6 picoseconds are given in the previous U.S. Pat. No. 4,855,749 in which a conventional laser is used. The result is that higher frequency excitations are achieved, and that it is frequently possible for emitter 1 and receiver 2 to be coincident if this is desirable; this would then mean that only a single antenna and micro-laser support substrate is necessary, to which all electrical and optical lines in FIG. 1 would lead; reception would then take place after emission. All that is necessary is that the path traveled by the emitted wave stream is a sufficiently long path so that the stream does not return to the emitter-receiver until after the emission has finished.

Figure 2:
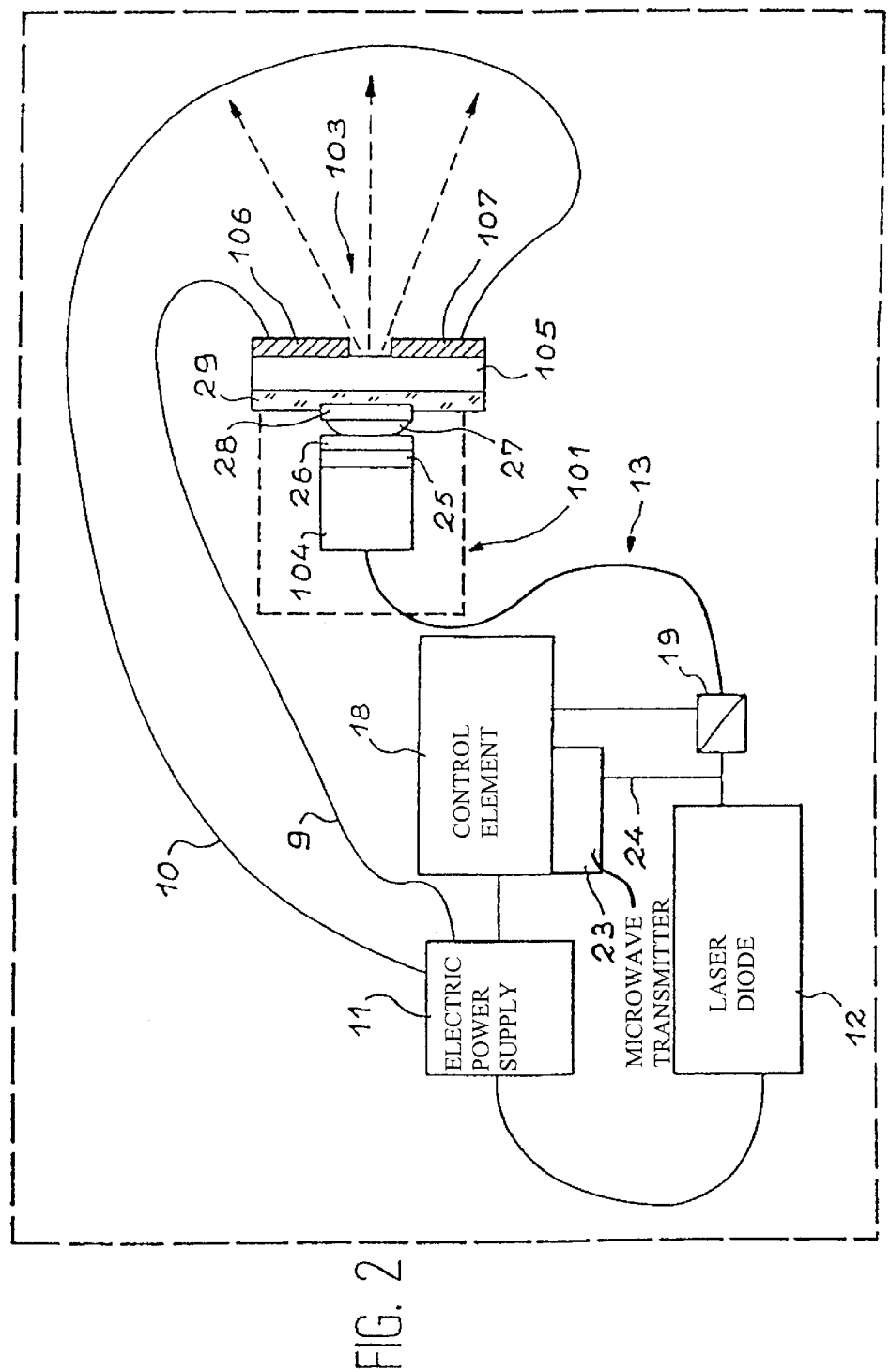
FIG. 2 illustrates some details of another embodiment of the invention.

FIG. 2 illustrates an emitting unit 101 for a slightly different embodiment of the equipment; the receiving unit may be built in the same way or with a signal sampler similar to that shown in FIG. 1 (in which it is also optional).

The antenna 103 is still deposited on a photo-conducting layer 105, and a micro-laser 104 is located behind this layer 105 from which it is separated by a stack of components; this stack comprises in sequence an optical trigger 25 in front of the micro-laser 104, a semi-reflecting layer 26, a micro-lens 27 or another light concentration device, an impedance adaptation layer 28 and finally a transparent and insulating layer 29 (that may be made of sapphire or silica) in contact with the photo-conducting layer 105 which acts as a substrate.

The optical trigger 25 is a bi(4-dimethylaminodithiobenzyl)nickel layer that provides the luminous power flux for the micro-laser 104 at the end of the layer stack; the semi-reflecting layer 26 prevents light from returning to micro-laser 104 and thus closes its oscillating cavity while avoiding radiation losses, damage to the control switchgear due to reflected light and even the ends of wave stream produced by double reflection and which would disturb the measurements; the micro-lens 27 concentrating light flux towards the area of interest of the photo-conducting layer 105 may be a polymer layer such as a melted "photoresist" resin described on pages 1322 to 1324 in the June 1993 issue of Optical Engineering; and the purpose of the impedance adaptation layer 28 is to eliminate reflections of light pulses from the micro-laser 104 produced in front of layer 29.

The micro-lens 27 replaces the ordinary lenses usually used with lasers to concentrate their beam on the target. Since it is integrated into the emitter 101 or the receiver 102, it cannot lose its settings. Concentration of the beam from micro-laser 4 between parts 6 and 7 of antenna 3 can moderate the total light intensity to be supplied, particularly in that the focal distance of the micro-lens 27 is very short. Note also that the intensity of the transmitted wave stream also depends very strongly on the material from which the photo-conducting layer 105 is made, and that silicon doped smith oxygen, which is conventional for this application, may advantageously be replaced by cadmium telluride and gallium arsenide as mentioned above, provided at least that they are manufactured by making them grow at low temperature so that they do not produce a single crystal; cadmium telluride is then formed in polycrystals, and gallium arsenide contains almost pure arsenic inclusions. These structural heterogeneities encourage mobility of electrons in the crystal and therefore conductivity. These advantages would be expected in other non-monocrystalline crystals, which are still easy to make by using a growth temperature that is too low for perfect annealing. Currents 100 times larger (100 pA instead of 1 pA) can be obtained in antenna 3 by using this type of material.

The separate conducting portions 106 and 107 of the antenna 103 are still strips placed side by side to define a bipole structure, or they may be spiral, helical, etc., depending on the application considered and the useful frequency band. In this case, the electromagnetic radiation is emitted perpendicular to the strips.

The control system is not modified with respect to FIG. 1, and the emitter 101 and receiver 102 may or may not be on the same support board.

Figure 3:
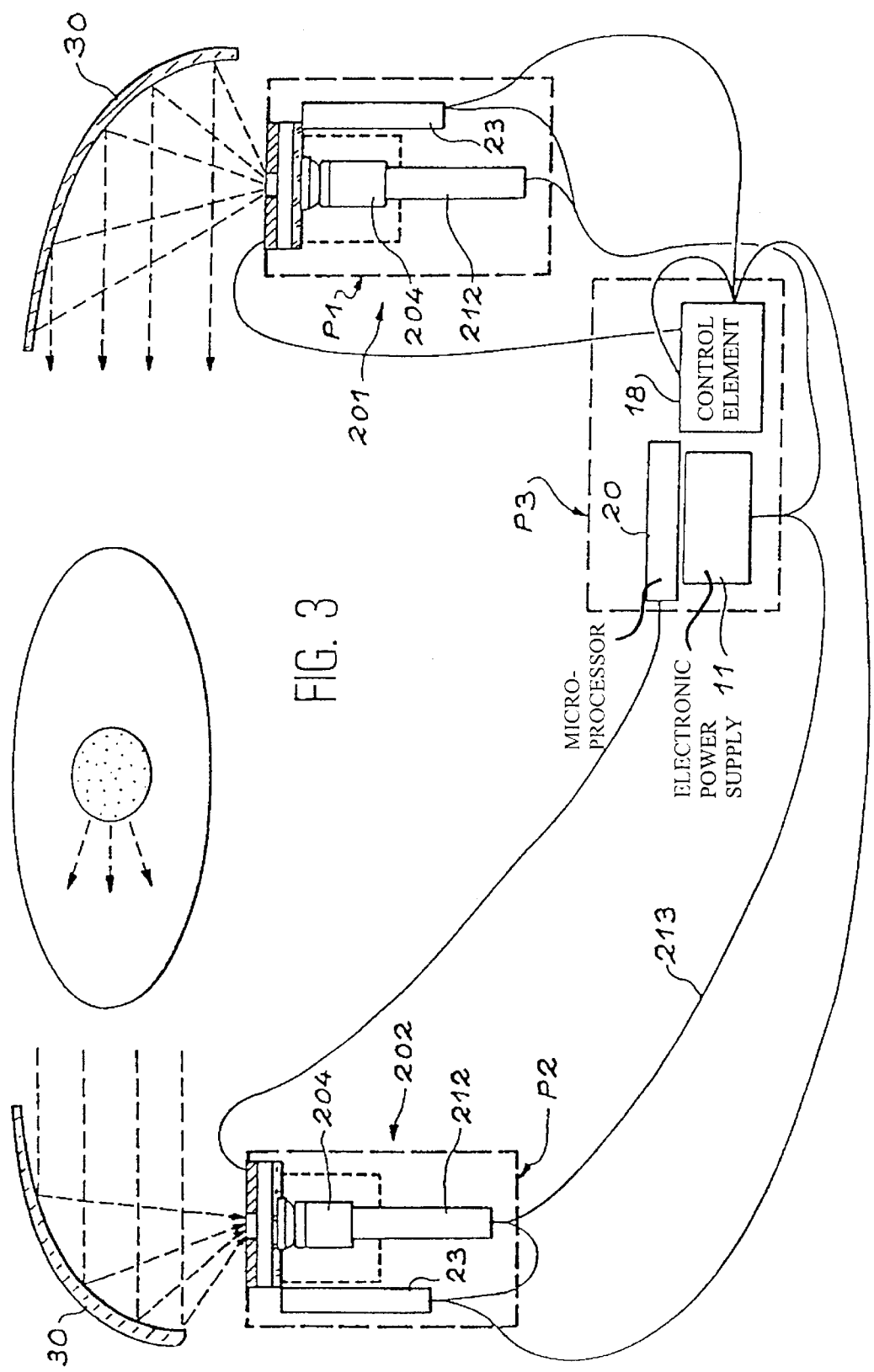
FIG. 3 is a view of another embodiment of the invention.

FIG. 3 shows that other modifications can be made to the equipment in FIGS. 1 and 2; emitter 201 and receiver 202 are firstly separated to enable the examination of an intermediate gaseous medium without any wave reflection in his medium (it will often be preferred to study solid media with a reflection of the wave stream; the device in FIG. 1 or a device in the combined emitter and receiver will then be used). The laser diode 12 can then be replaced by a pair of laser diodes 212, each of which is located immediately behind the micro-laser 204, and the optical guide in this case marked as reference 213 connects the electricity power supply 11 to each of the laser diodes 212. However this arrangement is not compulsory, and a single laser diode as shown in FIG. 1 could be used, which would be integrated either into the emitter support board (P1) or into the receiver support board (P2), or into a control components support board (P3). This optical guide would then be designed appropriately and could only comprise a single optical fiber connecting the emitter and receiver boards P1 and P2. Free emission of laser light from one board to the other would also be possible without an optical fiber. Electricity power supply, control and recording lines also depend on the precise layout of elements of the equipment.

The emitter 201, the receiver 202 and their antennas 3 can be aligned, so that the waves would be transmitted directly from one to another; as shown in the figure, it would also be possible to place parabolic or elliptical reflectors 30 in front of the antennas 3 to transform the divergent waves emitted by antennas 3 into parallel waves or waves focused otherwise passing through the medium being studied.

Note also that the photo-conducting layers and the antennas of emitter 201 and receiver 202 are laid out facing each other, or that the beams of micro-lasers 204 that excite them are approximately co-linear (taking account of reflections produced by reflectors 30); the advantage is that the wave stream emitted from emitter 201 spreads out approximately isotropically immediately after leaving emitter 201, passing through the gaseous medium being studied with a uniform front and arrives at receiver 202 at the same instant; this situation in FIG. 1, in which emitter 1 and receiver 2 are in the same plane, is different since the wave stream then has an X component that spreads out in the plane common to emitter 1 and receiver 2, and a Y component that spreads out in an orthogonal plane; these X and Y components propagate in the same Z direction as in the figure but they are slightly out of phase and therefore the signal produced is not as sharp as on receiver 202. This disadvantage needs to be considered and balanced with the ease of manufacture of the device in FIG. 1 with a single board P, before choosing this embodiment or the embodiment shown in FIG. 3.

FIG. 4 shows the shape of an electromagnetic wave stream emitted by the antenna from the emitting unit 1, 101 or 201 as a function of time. The Fourier transform of this wave stream shows that it can be decomposed into an extended frequency range (on the abscissas axis) as shown in FIG. 6. The signal received by the antenna of receiver 2, 102 or 202 and disturbed by attenuation or reflection through the medium being studied may be like that shown in FIG. 5. Its Fourier transform is given in FIG. 7; it is used in the normal manner and in particular may include absorption peaks revealing the state of the medium being studied and particularly the presence of some gases. The example shown represents two of these peaks at frequencies f1 and f2.

Finally, FIG. 8 illustrates an example of a single emitter-receiver 301 according to a previous part of this description; the emitter and receiver are combined, and the emitter-receiver has an antenna 303 composed of two metallic parts 306 and 307 on a photo-conducting layer 305, and a micro-laser 304 creates a short circuit between them; lines 9, 10, 14, 15 and 22 described with reference to FIG. 1 lead to it in the same way, and the rest of the equipment is identical to that shown in FIG. 1 except that the shielding 17 is omitted.

What is claimed is:

1. Wave emitter-receiver device for examining a medium through which waves pass, comprising, in combination, an emitter for emitting emitted waves and a receiver for receiving received waves after passing through said medium, said emitter and receiver, each having an antenna, wherein the emitter antenna and the receiver antenna each are formed of distinct portions laid out on separate photo-conducting layers; a wave generation support device comprising an electricity power supply connected to said portions of said emitter antenna and creating a potential difference between said portions of said emitter antenna; said wave generation support device also comprising a light source including a first micro-laser for supplying first light pulses to the photo-conducting layer of said emitter between said portions of said emitter antenna, said potential difference triggering said emitted waves if said photo-conducting layer of said emitter is illuminated by said light source; a signal reception support device comprising a second micro-laser for supplying second light pulses to the photo-conducting layer of said receiver between said portions of said receiver antenna; and a wave usage device for recording and analyzing said received waves, wherein the photo-conducting layers comprise a non-monocrystalline crystal.

2. Device according to claim 1, wherein the light source includes micro-lenses for concentrating light pulses between the photo-conducting layers and the micro-lasers.

3. Device according to claim 2, and further comprising anti-reflection layers inserted between the micro-lasers and the micro-lenses.

4. Device according to claim 3, and further comprising optical impedance adaptation layers inserted between the micro-lenses and the photo-conducting layers.

5. Device according to claim 1, wherein the crystal comprises cadmium telluride polycrystal.

6. Device according to claim 1, wherein the crystal comprises gallium arsenide crystal in which arsenic rich inclusions are formed.

7. Device according to claim 1, wherein the light pulses supplied have durations of less than 2 ps.

8. Device according to claim 7, wherein the emitter and the receiver are an integrated device having one antenna formed of distinct portions laid out on one photo-conducting layer and having one micro-laser, said integrated device acting as said emitter during a first time interval and acting as said receiver during a second time interval.

9. Device according to claim 1, wherein the light source comprises optical delay lines between said receiver and a laser.

10. Device according to claim 9, wherein the optical delay lines have different delays, and the signal reception device and the wave usage device comprise connection lines capable of sampling signals received by the receiver.

11. Device according to claim 1, and further comprising a reflector placed in a wave radiation path between the emitter antenna and the receiver antenna.

12. Device according to claim 1, wherein the emitter and the receiver are located on separate boards including an emitter board including the photo-conducting layer of the emitter, and a receiver board including the photo-conducting layer of the receiver.

13. Device according to claim 12, wherein the emitter and receiver boards face one another.

14. Device according to claim 1, wherein the emitter and the receiver are on separate photo-conducting layers and located side by side on a single board with electromagnetic shielding between them, and the emitter and the receiver antennas are oriented in parallel directions to each other.

15. Device according to claim 1, wherein said electricity power supply is further connected to said emitter.

16. Device according to claim 1, wherein the light source further comprises a laser and an alternating light cut-off and transmission gate.

17. Device according to claim 16, wherein the gate comprises a component that changes the optical index as a function of an electric field, said electric field being generated in an adjacent control element.

18. Device according to claim 1, wherein the light source further comprises a light guide network with a fork towards the emitter and the receiver, said fork comprising a first branch to the emitter and a second branch to the receiver.

19. Device according to claim 18, and further comprising means for varying the optical impedance of the light guide network.

* * * * *